United States Patent
Charlebois et al.

(10) Patent No.: US 12,214,093 B2
(45) Date of Patent: Feb. 4, 2025

(54) PATHOGEN REDUCED PLATELET COMPOSITIONS AND RELATED METHODS

(71) Applicant: SEXTON BIOTECHNOLOGIES, INC., Indianapolis, IN (US)

(72) Inventors: Steven Charlebois, West Lafayette, IN (US); Sreedhar Thirumala, Zionsville, IN (US)

(73) Assignee: SEXTON BIOTECHNOLOGIES, INC., Indianapolis, IN (US)

( * ) Notice: Subject to any disclaimer, the term of this patent is extended or adjusted under 35 U.S.C. 154(b) by 1193 days.

(21) Appl. No.: 16/227,094

(22) Filed: Dec. 20, 2018

(65) Prior Publication Data
US 2019/0269808 A1 Sep. 5, 2019

Related U.S. Application Data

(60) Provisional application No. 62/608,498, filed on Dec. 20, 2017.

(51) Int. Cl.
*A61L 2/00* (2006.01)
*A61K 35/19* (2015.01)
(Continued)

(52) U.S. Cl.
CPC .............. *A61L 2/007* (2013.01); *A61K 35/19* (2013.01); *A61K 35/28* (2013.01); *A61P 37/00* (2018.01);
(Continued)

(58) Field of Classification Search
CPC ..... A61L 2/007; A61L 2202/22; A61K 35/19; A61K 35/28; C12N 5/0644; C12N 5/0662;
(Continued)

(56) References Cited

U.S. PATENT DOCUMENTS

| 5,730,933 A | 3/1998 | Peterson |
| 10,946,046 B2 * | 3/2021 | Delorme ............... A61K 35/19 |

(Continued)

FOREIGN PATENT DOCUMENTS

| CN | 1344170 A | 4/2002 |
| CN | 1606457 A | 4/2005 |

(Continued)

OTHER PUBLICATIONS

Fertey et al. Pathogens Inactivated by Low-Energy-Electron Irradiation Maintain Antigenic Properties and Induce Protective Immune Responses. Viruses. Nov. 23, 2016;8(11):319 (Year: 2016).*

(Continued)

*Primary Examiner* — Blaine Lankford
*Assistant Examiner* — Lauren K Van Buren
(74) *Attorney, Agent, or Firm* — Brown & Michaels, PC

(57) ABSTRACT

Disclosed are methods for treating platelet compositions (e.g. platelet concentrates and/or platelet lysates) with electron beam radiation, where the compositions are in a frozen state during irradiation with the e-beam radiation. The methods can be conducted using e-beam radiation at doses effective to reduce the pathogen content of the compositions while retaining highly beneficial bioactivities of the compositions. Also disclosed are compositions preparable by the methods, and methods and compositions involving the use of the e-beam treated materials.

10 Claims, 6 Drawing Sheets

(51) Int. Cl.
| | |
|---|---|
| *A61K 35/28* | (2015.01) |
| *A61P 37/00* | (2006.01) |
| *C12N 5/0775* | (2010.01) |
| *C12N 5/078* | (2010.01) |

(52) U.S. Cl.
CPC ......... *C12N 5/0644* (2013.01); *C12N 5/0662* (2013.01); *A61L 2202/22* (2013.01); *C12N 2500/84* (2013.01); *C12N 2501/11* (2013.01); *C12N 2501/115* (2013.01); *C12N 2501/135* (2013.01); *C12N 2501/15* (2013.01)

(58) Field of Classification Search
CPC ............ C12N 2500/84; C12N 2501/11; C12N 2501/115; C12N 2501/135; C12N 2501/15
See application file for complete search history.

(56) References Cited

U.S. PATENT DOCUMENTS

| | | | |
|---|---|---|---|
| 2003/0161753 A1* | 8/2003 | MacPhee | A61M 1/3683 422/1 |
| 2009/0166178 A1 | 7/2009 | Harmon et al. | |
| 2017/0274055 A1* | 9/2017 | Babcock | A61K 38/54 |

FOREIGN PATENT DOCUMENTS

| | | |
|---|---|---|
| CN | 1665388 A | 9/2005 |
| CN | 1720064 A | 1/2006 |
| JP | 06113835 | 4/1994 |
| WO | 2004/050121 A1 | 6/2004 |
| WO | 2016193591 A1 | 12/2016 |

OTHER PUBLICATIONS

Furuta M, Suwa T, Kuwabara Y, Otsuhata K, Takeda A. Electron-beam sterilization of laboratory animal diets—sterilizing effect of 10-MeV electrons from a linear accelerator. Exp Anim. Jul. 2002;51(4):327-34. (Year: 2002).*

Chou, Ming-Li and T. Burnouf. "Current methods to manufacture human platelet lysates for cell therapy and tissue engineering: possible trends in product safety and standardization." ISBT Science Series 12 (Feb. 2017): pp. 168-175 (Year: 2017).*

International Search Report and Written Opinion received for PCT Patent Application No. PCT/US2018/066788, mailed on Feb. 20, 2019, 12 pages.

Laurence Corash: Inactivation of viruses, bacteria, protozoa, and leukocytes in platelet concentrates: Current research perspectives, Transfusion Medicine Reviews, vol. 13, No. 1, Jan. 1, 1999, pp. 18-30 (first page submitted).

Mohr et al., "Sterilization of platelet concentrates at production scale by irradiation with short-wave ultraviolet light: PC Sterilization By UVC Irradiation", Transfusion., vol. 49, No. 9, Sep. 1, 2009, pp. 1956-1963 (Abstract submitted).

Mrazova et al., "Comparison of structural changes in skin and amnion tissue grafts for transplantation induced by gamma and electron beam irradiation for sterilization", Cell And Tissue Banking, vol. 17, No. 2, Dec. 9, 2015, pp. 255-260 (Abstract submitted).

Schmidt et al., "Does sterilization with fractionated electron beam irradiation prevent ACL tendon allograft from tissue damage?", Knee Surgery, Sports Traumatology, Arthroscopy, Springer International, Berlin, DE, vol. 25, No. 2, Jul. 20, 2016, pp. 584-594 (Abstract submitted).

Viau et al., "Pathogen reduction through additive-free short-wave UV light irradiation retains the optimal efficacy of human platelet lysate for the expansion of human bone marrow mesenchymal stem cells", Plos One, vol. 12, No. 8, p. e0181406, XP055495757.

Masakazu Furuta, "Electron-beam Sterilization of Laboratory Animal Diets—Sterilizing Effect of 10-MeV Electrons from a Linear Accelerator"; 327-334 7-40 43-45; Jul. 2002.

Fertey et al. "Pathogens Inactivated by Low-Energy-Electron Irradiation Maintain Antigenic Properties and Induce Protective Immune Reponses" ; Viruses 2016.

Viau et al. "Pathogen reduction through additive-free short-wave UV light irradiation retains the optimal efficacy of human platelet lysate for the expansion of human bone marrow mesenchymal stem cells"; retrieved from https://journals.plos.org/plosone/article?id=10.1371/journal.pone.0181406Aug. 1, 2017.

* cited by examiner

PATHOGEN REDUCED PLATELET COMPOSITIONS AND RELATED METHODS

CROSS-REFERENCE TO RELATED APPLICATIONS

This application claims the benefit of U.S. Provisional Application No. 62/608,498, filed Dec. 20, 2017, which is hereby incorporated by reference.

BACKGROUND

Aspects of the present disclosure relate generally to processes effective to reduce pathogens in platelet compositions such as platelets or platelet lysates, and more particularly to methods that involve irradiation of such compositions under conditions effective to reduce pathogens while retaining beneficial biological activities.

As further background, biologic materials are increasingly being used or explored for use in research and medical applications. Biologic materials are desirable in many applications because they contain numerous bioactive factors that are beneficial in supporting cell growth and that can be therapeutic when administered to patients. However, biologic materials also present risks in use because they can contain pathogens, for example viruses, derived from a human or other animal donor for the materials.

Numerous techniques have been explored for treating biologic materials to reduce their level of pathogens. A difficulty arises in that, in addition to reducing pathogen levels, the techniques can degrade desired biological activities of the materials. Needs therefore exist for methods for reducing pathogens in biologic materials such as platelet compositions, that can be conveniently carried out, that effectively reduce the level of pathogens, and that provide a treated material that retains beneficial biologic activity. Aspects of the present disclosure are addressed to these needs.

SUMMARY

In certain aspects, the present disclosure provides methods for making pathogen reduced compositions that include irradiating a composition comprising a platelet concentrate or a platelet lysate while in a frozen state with electron beam ("e-beam") radiation. The methods can include applying the e-beam radiation at doses effective to reduce the level of pathogens in the composition while maintaining amounts of bioactive factors, for example bioactive growth factors, in the composition. The methods can be conducted using irradiation with e-beam at a dose effective to achieve at least a 3-Log reduction in viruses in the composition while maintaining a substantial percentage, for example greater than 50%, of one or more growth factors of the composition. The one or more growth factors can include FGFb, EGF, PDGF-AB, PDGF-BB and/or TGF-β. In certain embodiments, the methods can also include applying cooling to the frozen composition during the irradiating. The frozen composition can be at a temperature below about −20° C., more preferably below about −40° C., at the commencement of the irradiating, and in some embodiments can be maintained at such temperatures during the irradiating.

In other aspects, the present disclosure provides pathogen reduced platelet lysate compositions. The pathogen reduced platelet lysate compositions can be e-beam treated compositions and can have a growth factor profile including FGFb at a level of at least 50 pg/ml, EGF at a level of at least 1000 pg/ml, PDGF-AB at a level of at least 10 ng/ml, PDGF-BB at a level of at least 1 ng/ml, and/or TGF-β at a level of at least 20 ng/ml. The compositions can have measurable levels of e-beam-induced protein modifications. For example, the compositions can have levels of fragments of a given protein and/or levels of aggregates of a given protein, e.g. where the given protein is albumin, that are greater than those which occur in the corresponding composition except without having been subjected to the e-beam radiation.

In other aspects, the present disclosure provides methods of culturing cells which comprise culturing cells in the presence of a pathogen reduced platelet lysate composition as described above or elsewhere herein. In further aspects herein, such cultured cells can be administered to patients in methods of medical treatment.

In still further aspects, the present disclosure provides methods for treating patients that include administering to a patient a platelet composition (e.g. a platelet lysate) as described above or elsewhere herein.

Additional aspects of the present disclosure, as well as features and advantages thereof, will be apparent to those of ordinary skill in the art from the descriptions herein.

A: Cell growth analysis using cell number B: Cell growth analysis using percentage of control (*=p<0.05, =p<0.001, *=p<0.0002, ****=p<0.0001).

Figure 9:
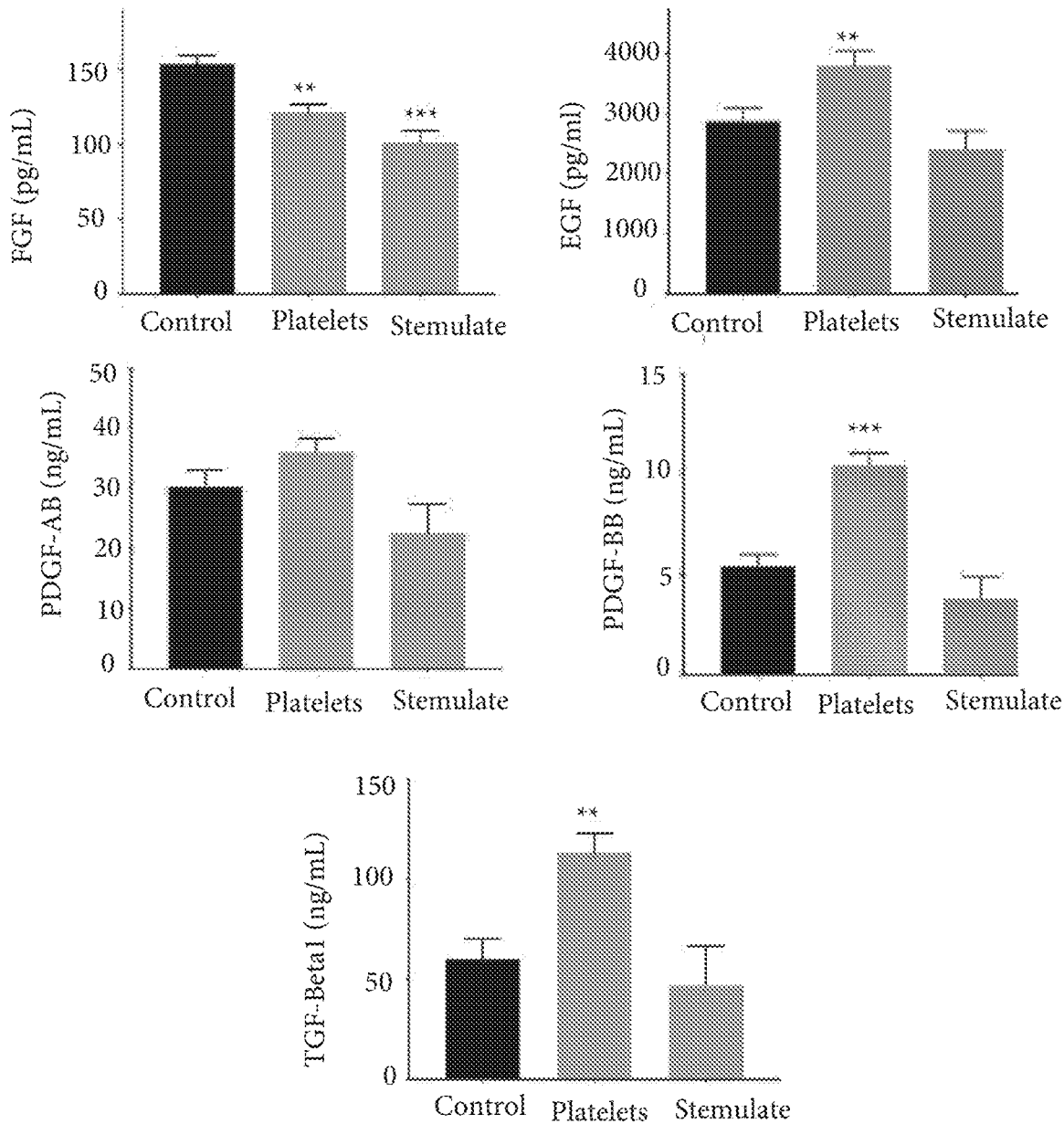

FIG. 9 shows ELISA measurements of the concentrations of five growth factors (FGFb, EGF, PDGF-AB, PDGF-BB, and TGF-beta) in HPL processed from e-beamed platelets and e-beamed HPL, versus a non-e-beamed control. Data reported are the mean of three independent experiments (*=p<0.05, =p<0.001, *=p<0.0002, ****=p<0.0001).

DETAILED DESCRIPTION

While the present invention may be embodied in many different forms, for the purpose of promoting an understanding of the principles of the present invention, reference will now be made to embodiments, some of which are illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates. Additionally, in the detailed description below, numerous alternatives are given for various features related to the structure or composition of materials, or to modes of carrying out methods. It will be understood that each such disclosed alternative, or combinations of such disclosed alternatives, can be combined with the more generalized features discussed in the Summary above, or set forth in the Listing of Certain Embodiments below, to provide additional disclosed embodiments herein.

As disclosed above, certain aspects of the present disclosure relate to methods for making pathogen reduced compositions that include irradiating a frozen composition comprising a platelet concentrate or a platelet lysate with electron beam ("e-beam") radiation, to compositions that are obtainable by such methods, and to methods of use of the pathogen reduced compositions for example in the culture of cells or in the treatment of patients.

The composition to be treated with e-beam radiation can contain intact platelets, e.g. as in a platelet concentrate composition, or can be a platelet lysate composition, or can include a mixture including a platelet concentrate and platelet lysate. These compositions are sometimes together referred to herein as "platelet compositions". Platelet concentrate compositions used in the disclosed methods may be obtained in any suitable way. As used herein, the term platelet concentrate refers to a liquid composition containing platelets at a level of about $1 \times 10^9$ or greater. The concentration of platelets in the platelet concentrate is preferably at least about $1 \times 10^{10}$ platelets/ml. Particularly preferred are platelet concentrates, especially apheresed platelet concentrate units (expired or non-expired), that have a concentration of platelets in the range of about $1 \times 10^9$ to about $1 \times 10^{12}$ platelets/ml. The platelet concentrate can be derived from a blood source, where the blood source is preferably human blood, such as whole human peripheral blood. When derived from blood or otherwise, the platelet concentrate will preferably be essentially free from red blood cells, i.e. having fewer than about $1 \times 10^6$ red blood cells/ml, and preferably having fewer than about $1 \times 10^5$ red blood cells/ml. The platelet concentrate in some embodiments includes both platelets and plasma proteins, and may be provided by platelet units obtained from whole peripheral blood of human donors by apheresis. It is envisioned that whole blood from other species, for example mammalian species, may also be used as a source for platelet concentrates to be processed as described herein. In certain embodiments, platelet units from multiple different human or other donors can be pooled at some point during processing to obtain a composition to be processed as described herein. In typical practice today, each human donor apheresed platelet unit has a volume of about 100 to about 500 mL, more typically about 100 to 400 mL, and contains about 100 to $500 \times 10^9$ platelets along with plasma isolated with the platelets during the apheresis procedure. Donated human apheresis platelet units have a relatively brief shelf life for use at health care facilities, typically about five days. Platelet units used in methods herein can be recently expired human apheresis platelet units obtained from health care facilities, and can optionally be stored frozen at any suitable temperature, for example about −20° C., prior to use as described herein.

In preparing a platelet lysate, the contents of the platelets can be released by a suitable method. In some modes, the platelets are lysed by subjecting them to at least one freeze-thaw cycle to release the platelet contents, and optionally multiple freeze-thaw cycles (e.g. 2 or 3 freeze-thaw cycles). In use of a freeze-thaw cycle, the platelet concentrate can be frozen at any suitable temperature. In some aspects, the platelet concentrate is frozen at a temperature between about −10° C. and about −80° C. In specific preferred embodiments, the platelet concentrate is frozen at about −20° C. To lyse the platelets, the frozen platelet concentrate is thawed, for example in a 37° C. water bath or by other effective means, to form a "raw" platelet lysate composition. The raw platelet lysate contains the lysed platelet membranes, growth factors and other substances released from the lysed platelets. When the platelet concentrate being thawed contains plasma along with the platelets, the platelet lysate will also contain plasma, including plasma proteins therein. Other techniques for releasing platelet contents, for example activation with thrombin, may also be used to prepare a platelet lysate for use as described herein. However, freeze-thaw or other mechanical techniques for lysing the platelets are considered advantageous in that they do not require the addition of a non-native protein (e.g. thrombin) to the platelet concentrate, which addition both increases cost and leads to the presence of at least some of the thrombin in the downstream processed material. A "raw" platelet lysate as thus described can be subjected to e-beam treatment as described herein. However, in other embodiments, the raw platelet lysate has been processed to remove amounts of certain components, notably fibrinogen, prior to being subjected to the e-beam treatment.

The raw platelet lysate contains multiple growth factors from the platelet concentrate starting material. These can include, for example, transforming growth factor beta 1 (TGF-β1), epidermal growth factor (EGF), basic fibroblast growth factor (FGFb), platelet derived growth factor AB (PDGF-AB), and platelet derived growth factor BB (PDGF-BB).

In certain embodiments, the raw platelet lysate includes the following growth factors and amounts thereof (based on the volume of original, undiluted platelet concentrate):
- about 20,000 to about 150000 pg/ml TGF-β1, preferably about 70000 to about 120000 pg/ml TGF-β1; and/or
- about 100 to 600 pg/ml EGF, preferably about 200 to about 600 pg/ml EGF; and/or
- about 5 to about 250 pg/ml FGFb, preferably about 50 to 200 pg/ml FGFb; and/or
- about 10 to about 70 ng/ml PDGF-AB, preferably about 40 to about 65 ng/ml PDGF-AB; and/or about 1 to about 20 ng/ml PDGF-BB, preferably about 2 to about 15 ng/ml PDGF-BB; and/or about 400 to 1100 pg/ml SDF-1α, preferably about 500 to about 1000 pg/ml SDF-1α; and/or about 10 to about 800 pg/ml VEGF, preferably about 100 to about 600 pg/ml VEGF.

In preferred forms, the raw platelet lysate also includes one or more components derived from plasma in the platelet concentrate starting material, including for example fibrinogen, globulins, albumen, triglycerides, glucose, sodium, calcium, and/or cholesterol. In preferred forms, the raw platelet lysate includes the following components and amounts:

about 0.5 to 2.5 g/dL globulins, preferably about 1.5 to 2.5 g/dL globulins; and/or about 2 to 5 g/dL albumin, preferably about 3 to 4 g/dL albumin; and/or about 100 to 200 mmol/L sodium, preferably about 120 to about 160 mmol/L sodium; and/or about 40 to 200 mg/dL triglycerides, preferably about 50 to 120 mg/dL triglycerides; and/or about 150 to 300 mg/dL glucose, preferably about 150 to 250 mg/dL glucose; and/or about 5 to 12 mg/dL calcium, preferably about 6 to 10 mg/dL calcium; and/or about 1 to 3.5 million ng/mL fibrinogen, preferably about 1.5 to 2.5 million ng/mL fibrinogen.

The raw platelet lysate can also contain other bioactive substances, for example one or more interleukins, interferons, and/or tumor necrosis factors. These interleukin(s), interferon(s) and/or tumor necrosis factor(s) may include, for example, one, some, or all of interleukin (IL)-1b, IL-6, IL-8, IL-10, IL-13, IL-17, interferon-gamma (IFN-gamma), and tumor necrosis factor-alpha (TNF-alpha).

In certain embodiments herein, the raw platelet lysate is processed to remove particulate matter, for example filtered one or more times and/or centrifuged. Such filtration can, for example, include passing the raw platelet lysate through a sterile filter.

As discussed above, in some embodiments herein, the raw platelet lysate is treated to recover a fraction thereof with a reduced fibrinogen concentration as compared to the raw platelet lysate. Fibrinogen may be removed by any suitable technique, including for example by conversion to fibrin resulting in the formation of solid clot material, which can be separated from a platelet lysate liquid. Such conversion to fibrin can be induced by the addition of a clotting agent. In accordance with some forms of practicing the disclosed methods, a clotting agent, for example a calcium chloride salt, can be added to the raw platelet lysate. Illustratively, a calcium chloride salt can be added to the raw platelet lysate in an amount between about 0.1 g and 2 g per liter of raw platelet lysate. In preferred embodiments, about 0.4 g to about 0.75 g of a calcium chloride salt is added per liter of raw platelet lysate. The combined platelet lysate and calcium chloride or other clotting agent may be placed on a shaker or otherwise agitated to ensure thorough mixing of the clotting agent with the concentrate. The resulting mixture can then be allowed to form a solid clot material, in certain embodiments for a period of at least about 8 hours, or at least about 12 hours, and typically in the range of about 8 hours to about 36 hours. In some forms, at least a predominant amount (over 50%) of the resulting clotted material, and potentially at least 80% or at least 90% of the resulting clotted material, is constituted by a substantially homogenous clot gel. Such a substantially homogenous clot gel can exhibit a consistent gel phase throughout the material, with liquid entrained within a continuous fibrin matrix. In other forms, the clotted material can occur as a multitude of discrete solid clot particles suspended in a liquid phase.

After the solid clotted material has formed, liquid material can be separated therefrom. Any suitable technique may be used for this purpose. In preferred forms where at least a predominant amount (over 50% by weight and potentially at least 80% or at least 90% by weight) of the clotted material is constituted by a substantially homogenous clot gel, the clotted material is pressed between two or more surfaces to separate clotted solids from liquid. Such pressing can express the liquid from the gel material while compressing and condensing the fibrin matrix of the gel. Pressing the clotted material can in some forms be conducted in a flexible container such as a plastic bag. The clot gel can be pressed, for example manually by hand or by forced application of an implement, to one region (e.g. end) of the bag or other flexible container and the liquid expressed from the solid fibrin matrix can gather in another region (e.g. end) of the bag or other flexible container. A second bag or other container can be connected to the first bag in which the pressing occurs, either during or after the pressing, and the liquid material can be transferred to the second bag or other container. In other modes, the clot gel can be in a rigid container such as a bucket, and can by pressed by hand or with the forced application of an implement to express the liquid from the solid fibrin matrix and compress and condense the fibrin matrix. In other forms, where the clotted material occurs as a multitude of discrete solid clot particles suspended in a liquid phase, the composition can be centrifuged to concentrate the clot particles into a solid mass, and the solid mass can be separated from the resulting liquid phase. It will be understood that combinations of these and/or other techniques can be used in the separation of clotted material from liquid material in the preparation of platelet lysates for use as described herein.

After clotting and separation of the liquid and solid materials of the clotted raw platelet lysate, the separated platelet lysate liquid has a reduced concentration of fibrinogen as compared to the raw platelet lysate prior to clotting. In preferred forms, the raw platelet lysate has a fibrinogen content of at least one million ng/mL, typically in the range of about 1,500,000 to 3,500,000 (1.5 to 3.5 million) ng/mL, and after clotting and separation, the fibrinogen-depleted platelet lysate has a fibrinogen content of less than about 50,000 ng/mL, preferably less than about 20,000 ng/mL, and more preferably less than about 5,000 ng/mL. Illustratively, the fibrinogen-depleted platelet lysate can have a fibrinogen content in the range of about 500 ng/mL to about 20,000 ng/mL, or about 500 ng/mL to about 10,000 ng/mL, or about 500 ng/mL to 5000 ng/mL. Additionally or alternatively, the fibrinogen-depleted platelet lysate can contain less than about 5% of the fibrinogen present in the raw platelet lysate prior to clotting, preferably less than about 2%, and more preferably less than about 1%. As well, the fibrinogen-depleted platelet lysate can constitute at least about 70% of the volume of the raw platelet lysate, preferably at least about 75%, and typically in the range of about 75% to about 90%.

The fibrinogen-depleted platelet lysate recovered after the clotting of the raw platelet lysate and the liquid solid/separation contains multiple growth factors from the raw platelet lysate. These can include TGF-β1, EGF, FGFb, PDGF-AB, and PDGF-BB. In certain embodiments, this fibrinogen-depleted platelet lysate includes the following growth factors and amounts thereof from the raw platelet lysate:

about 20 to about 150 ng/ml TGF-β1, preferably about 25 to about 150 ng/ml TGF-β1; and/or about 1000 to about 4000 pg/ml EGF, preferably about 2000 to about 3500 pg/ml EGF; and/or about 50 to about 200 pg/ml FGFb, preferably about 75 to about 200 pg/ml FGFb; and/or about 10 to about 50 ng/ml PDGF-AB, preferably about 15 to about 40 ng/ml PDGF-AB; and/or about 1 to about 15 ng/ml PDGF-BB, preferably about 2 to about 15 ng/ml PDGF-BB.

In preferred forms, this fibrinogen-depleted platelet lysate also includes one or more components derived from plasma in the platelet concentrate starting material, including for example globulins, albumen, triglycerides, glucose, sodium, and/or calcium. Where a calcium chloride salt is used to clot the raw platelet lysate, the calcium present in the fibrinogen-depleted platelet lysate can be from both the raw platelet lysate and the added calcium salt. In certain embodiments, this separated liquid platelet lysate includes the following components and amounts:

about 0.5 to 2.5 g/dL globulins, preferably about 1 to 2 g/dL globulins; and/or about 2 to 5 g/dL albumin, preferably about 3 to 4 g/dL albumin; and/or about 100 to 200 mmol/L sodium, preferably about 120 to about 160 mmol/L sodium; and/or about 40 to 70 mg/dL triglycerides, preferably about 50 to 65 mg/dL triglycerides; and/or about 150 to 300 mg/dL glucose, preferably about 150 to 250 mg/dL glucose.

As well, where a calcium chloride salt is used as a clotting agent for the raw platelet lysate, the fibrinogen-depleted platelet lysate can in some forms include calcium at a level of about 15 to 35 mg/dL, and preferably about 15 to 25 mg/dL.

In accordance with some modes of manufacture, the fibrinogen-depleted platelet lysate is passed through a sterile filter prior to being treated with e-beam radiation as described herein. In preferred embodiments the sterile filter comprises a 0.2 μm sterile filter. Additionally or alternatively, the fibrinogen-depleted platelet lysate can be subjected to other treatments prior to the e-beam irradiation, including for example depth filtration and/or other pathogen reduction processes which can be orthogonal to the e-beam irradiation, for example a solvent-detergent pathogen reduction process in which the platelet lysate is treated with a liquid medium containing a solvent and a detergent (e.g. a nonionic detergent).

In some forms, the platelet composition (e.g. platelet lysate) to be subjected to the e-beam processing herein can have a total protein content of at least about 3 g/dL, and in some forms in the range of about 3 to about 6 g/dL.

Pathogens that may be present in the platelet composition include, as examples, viruses, bacteria, fungi, protozoa, parasites, and prions. Typical viruses that may be present, particularly in platelet compositions obtained from human donor sources, include syphilis, hepatitis B and C, human immunodeficiency virus 1 and 2, Human T-Cell lymphotropic virus I and II, and West Nile Virus. In accordance with embodiments herein, e-beam irradiation can be used to apply an e-beam dose effective to deplete one, some or all of these pathogens in the platelet composition (e.g. platelets and/or platelet lysate).

As disclosed above, for the e-beam processing, the platelet composition will be provided in a frozen state. In beneficial forms, the frozen platelet composition can be in the form of a body which can a length, a width, and a thickness, and first and second opposed faces between which the thickness is defined. In preferred embodiments, the body will have a maximum thickness of about 5 cm or less, about 3 cm or less, or in some variants about 2 cm or less. In additional or alternatively, the body can have an average thickness of about 5 cm or less, about 3 cm or less, or in some variants about 2 cm or less, in each case optionally having an average thickness of about 0.2 cm or more. As well, beneficial e-beam radiation treatment can occur when the body has a substantially uniform thickness. Thus, in some embodiments, over a contiguous segment of the body that constitutes at least 70% of the body, or at least 80% of the body, the body can have a thickness from the first to the second face that varies by no more than 30% (i.e. the thickness of the thickest location is no more than 1.3 times the thickness of the thinnest location), or in some forms by no more than 20%. In certain embodiments, such a contiguous segment of the body of frozen platelet composition can have a thickness that varies by no more than 10%. It will be understood, however, that other arrangements for the frozen platelet composition can be used in other embodiments described herein.

The platelet composition in the frozen state, e.g. in the form of a body as discussed above, can be contained within a container, such as a bag (e.g. a cryobag) or tray, which can be a closed container. In some embodiments the volume of the platelet composition in the container will be at least about 50 ml, or at least about 100 ml, and typically in the range of about 50 ml to about 10 L and more typically about 100 ml to about 5 L. To prepare this construct, the platelet composition can be introduced into the container in a liquid (unfrozen) state, and thereafter frozen. Prior to freezing, and especially where a body having uniform thickness properties as discussed above is desired, the liquid can be caused to assume the shape ultimately desired for the frozen platelet composition. With a container having deformable walls, such as a bag, the walls can be manipulated to deform them and conform the liquid-form platelet composition to the shape desired for the frozen state composition. If necessary or desired, forms, molds or other physical barriers external of the deformable walled container (e.g. bag) can be used to facilitate constraining and holding the liquid-form platelet composition to the shape ultimately desired for the frozen composition. Once the desired shape has been imparted to the composition in liquid form, the composition can be frozen to the shape to be subjected to the e-beam irradiation.

The platelet composition can be converted from a liquid composition to a frozen composition by any suitable means. These include, for example, exposing the liquid platelet composition to freezing temperatures e.g. in a mechanical freezer or by immersion in a cold liquid such as liquid nitrogen.

The frozen platelet composition can in some modes of operation be at a temperature of about −20° C. or below upon commencement of the e-beam irradiation. Preferably, this temperature will be about −40° C. or below, and more preferably about −60° C. or below. Optionally, in these or other cases, the frozen platelet composition at the commencement of the e-beam irradiation will be at a temperature of no lower than about −200° C. In some embodiments, the temperature of the frozen platelet composition will remain within these temperature ranges during the entire period of e-beam radiation. In such processes, while some temperature increase may occur during irradiation with the e-beam radiation, the temperature can nonetheless remain within the stated ranges.

A variety of suitable e-beam sterilization apparatuses are commercially available and can be used in the conduct of methods herein. One suitable such apparatus is commercially available under the tradename Impela® Electron Beam Accelerator (Iotron Industries, Inc.). The e-beam irradiation can be carried out in a conventional manner, for example by exposing the frozen platelet lysate composition, within a container such as a glass or plastic container, to an electron beam. For example, the container containing the frozen platelet composition can be placed on a conveyor which then passes through the electron beam, which is usually a focused beam. In some forms, the frozen platelet composition is exposed to the electron beam only a single time. In other forms, after treating a first side of the frozen platelet composition (e.g. a frozen body face as described above) with the e-beam, e.g. by passing the composition through the electron beam with the first side closest to the beam source, a second side of the frozen platelet composition (e.g. a frozen body face as described above) is treated with the e-beam, e.g. by again passing the composition through the electron beam with the second side closest to the beam source.

In typical applications, the energy level of the electron beam is about 5 to about 15 MeV, more typically about 8 to about 12 MeV. The time of exposure to the beam is typically proportional to the dimensions of the frozen platelet lysate composition, and will generally be in the range of about 30 seconds to about 10 minutes. The radiation dose delivered to the frozen platelet composition will typically be in the range of about 10 kGy to about 100 kGy, more typically about 20 kGy to about 80 kGy, and most typically about 30 kGy to about 70 kGy. In addition or alternatively, the radiation dose delivered can be a dose which is effective to achieve at least a 3-Log reduction, or at least a 5-Log reduction, in the level of one or more viruses. In other considerations, substantial uniformity of delivered dose throughout the frozen platelet lysate product, and thus a low "max/min ratio" (the ratio of the maximum dose received by any portion of the composition to the minimum does received by any portion of the composition), can be used. In some forms, the max/min dose ratio for the e-beam irradiation treatment of the platelet lysate composition is about 2:1 or lower, more preferably about 1.5:1 or lower, and even more preferably about 1.3:1 or lower.

During the e-beam irradiation, in certain embodiments, cooling is applied to the frozen platelet composition. This can, for example, be accomplished by placing the frozen platelet composition or container containing it against an object or within an environment as cold as, or colder than, the frozen platelet composition. In one form, a first side of a bag or other container containing the frozen platelet composition can be placed upon a slab or other mass of dry ice (frozen carbon dioxide, at about −78.5° C.), and the frozen platelet composition/dry ice combination passed through the electron beam to irradiate a second side of the container opposite the first side. For processes in which a bilateral treatment is desired, after such a first pass through the electron beam, the bag or other container can be inverted to place the second side against the dry ice, and the frozen platelet lysate/dry ice combination can be processed again through the electron beam to irradiate the first side of the bag or other container. It will be understood that similar processes can be conducted using a cold mass other than dry ice (e.g. a metallic article, a ceramic article, or another frozen substance) that is at a temperature equal to or below that of the frozen platelet composition, for example in the range of about −20° C. to about −200° C. or about −50° C. to about −200° C. Additionally, it will be understood that the side of the container that is closest to the e-beam (opposite the side against the dry ice or other cold mass) can in some embodiments be directly exposed to the electron beam uncovered by any amount of the dry ice or other cold mass. As well, the e-beam processing may be conducted with the frozen platelet lysate composition in a mechanically refrigerated gaseous environment, for example by including all or a portion of the e-beam processing equipment in the mechanically refrigerated gaseous environment.

Figure 1:
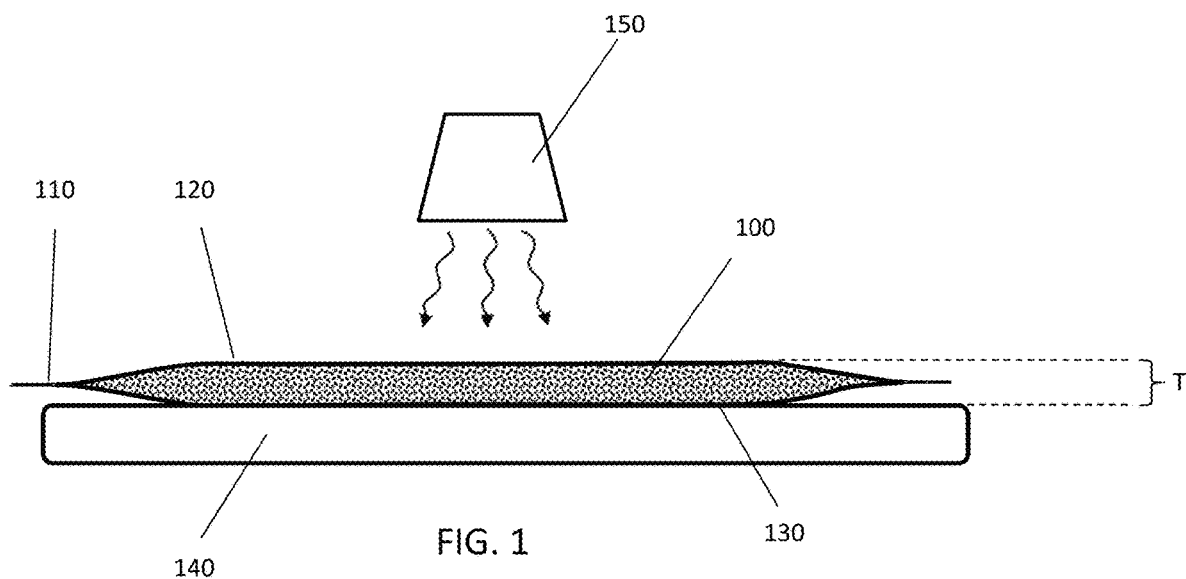
FIG. 1 provides a schematic view of one embodiment of a method for irradiating a platelet composition with e-beam radiation.

One arrangement for e-beam processing of the platelet composition is schematically illustrated in FIG. 1. As shown, a frozen platelet composition 100 (e.g. platelet concentrate, platelet lysate, or mixture thereof) is contained within a bag 110 having a first side 120, a second side 130, and a maximum thickness "T" between the sides 120 and 130. Second side 130 of bag 110 is positioned against a volume of dry ice 140, which will cool (transfer negative thermal energy to) the platelet composition 100 during treatment with the e-beam radiation. First side 120 of bag faces a source of e-beam radiation 150. Dry ice 140 and bag 110 can, if desired, be in a secondary container (not shown), which can be positioned on a conveyor (not shown) to pass the bag 110 and dry ice 140 through the e-beam emitted by source 150. In some embodiments, as discussed elsewhere herein, the bag 110 can be irradiated by source 150 on each of sides 120 and 130. To do this, after a first passage through the e-beam from source 150, the bag 110 can be inverted so that second side 130 is facing source 150 and first side 120 is positioned against dry ice 140. In this position, bag 110 and dry ice 140 can again be passed through the e-beam emitted by source 150.

It has been discovered that significant amounts of the biological activity of the platelet composition can be retained through the e-beam irradiation processing as described herein. In particular, e-beam processed frozen platelet lysate, and platelet lysate prepared from e-beam processed frozen platelet concentrate, demonstrate significant retained levels of ability to promote the proliferation of viable cells in culture when compared to a corresponding platelet lysate that has not been subjected to the e-beam processing, as described further in illustrative Examples 1 and 2 below. As well, e-beam processed frozen platelet lysate, and platelet lysate prepared from e-beam processed frozen platelet concentrate, retain significant levels of growth factors when compared to corresponding platelet lysate that has not be subjected to the e-beam processing. In some embodiments, the e-beam processed frozen platelet lysate or the platelet lysate prepared from e-beam processed frozen platelet concentrate will retain at least about 50% of at least one growth factor as compared to a corresponding non-e-beam processed platelet lysate. The at least one growth factor can, for example, be one, some or all of TGF-β1, EGF, FGFb, PDGF-AB, and PDGF-BB.

In certain embodiments, the e-beam treated platelet lysate, or the platelet lysate prepared from the e-beam treated platelet concentrate, has the following growth factor profile:
  TGF-β1 at a level of at least about 20 ng/ml, typically in the range of about 20 to about 150 ng/ml, preferably about 25 to about 150 ng/ml; and/or
  EGF at a level of at least about 1000 pg/ml, typically in the range of about 1000 to about 4000 pg/ml EGF, preferably about 2000 to about 3500 pg/ml; and/or
  FGFb at a level of at least about 50 pg/ml, typically in the range of about 50 to about 200 pg/ml, preferably about 75 to about 200 pg/ml; and/or PDGF-AB at a level of at least about 10 ng/ml, typically in the range of about 10 to about 50 ng/ml, preferably about 15 to about 40 ng/ml; and/or PDGF-BB at a level of at least about 1 ng/ml, typically in the range of about 1 to about 15 ng/ml, preferably about 2 to about 15 ng/ml.

In addition or alternatively to the above-stated growth factor profile, an e-beam treated platelet lysate can retain at least the following percentages of growth factor contents as compared to the growth factor contents prior to treatment with e-beam:

TGF-β1: at least about 60%, and typically in the range of about 60% to about 90%; and/or FGFb: at least about 50%, and typically in the range of about 50% to about 90%; and/or EGF: at least about 50%, and typically in the range of about 50% to about 80%; and/or PDGF-AB: at least about 50%, and typically in the range of about 50% to about 80%; and/or PDGF-BB: at least about 50%, and typically in the range of about 50% to about 80%;

The e-beam treated platelet composition can have the above-specified levels of growth factors and/or retained percentages of growth factors even after treatment with the e-beam at a does effective to achieve at least a 3-Log reduction, or at least a 5-Log reduction, or at least a 6-Log reduction, of one or more viruses in the platelet composition, for example Bovine Viral Diarrhea Virus, and/or even after treatment with a dose of e-beam radiation in the range of 20 to 100 kGy, or 30 to 70 kGy. It will be understood that disclosure herein of the use of a dose of e-beam radiation effective to achieve a specified Log reduction in a virus, does not mean that the composition being treated necessarily has such virus within it (although it can) or achieves such a reduction of the virus (although it can). This usage references the dose of e-beam radiation applied, and that it would be effective to achieve the specified Log reduction if the virus were homogenously distributed throughout the composition being treated.

The e-beam treated compositions herein, or compositions derived from them, can have identifying characteristics induced by the e-beam irradiation. For example, e-beam irradiation is known to cause fragmentation and/or aggregation of proteins in biological materials as compared to the corresponding materials that have not been exposed to the e-beam irradiation. In some forms, the platelet compositions can contain an amount of albumin (e.g. from blood serum sourced with the platelets), and the e-beam treated platelet composition can have an increased level of albumin fragments and/or albumin aggregation as compared to the corresponding platelet composition that has not been treated with the e-beam. As well, e-beam induced reductions in measured growth factor levels noted above are expected to occur in conjunction with e-beam induced changes in the growth factors that cause them to lose their biological activity. Accordingly, inactivated amounts of these growth factors (e.g. due to fragmentation, aggregation, improper folding and/or other causes) can also serve as a characterizing feature. Accordingly, in some forms the platelet composition can have the following e-beam-inactivated amounts of the following growth factors:

Inactivated FGFb at a level of at least about 10 pg/ml; and/or

Inactivated EGF at a level of at least about 50 pg/ml; and/or

Inactivated PDGF-AB at a level of at least about 3 ng/mL; and/or

Inactivated PDGF-BB at a level of at least about 0.5 ng/mL; and/or

Inactivated TGF-β at a level of at least about 0.5 ng/mL.

After the e-beam treatment, in certain modes, the pathogen reduced platelet composition can be introduced into a package or packages, preferably after thawing the frozen platelet composition to form a liquid composition. This is preferably conducted in a sterile transfer operation. For these purposes, the bag or other container in which the platelet composition resides for the e-beam treatment can have sterile connectors, for sterile connection to the interior of the bag/container and transfer of the contents to one or more package containers such as bags, vials, or the like. This direct packaging after e-beam treatment, without further steps that significantly alter the e-beamed platelet composition, is particularly applicable where the e-beam processing is conducted on a platelet lysate.

Where the e-beam processing is conducted on a composition comprising a platelet concentrate, the resulting e-beam treated composition will typically be subjected to further processing steps, in some modes to processing steps to prepare a platelet lysate from the e-beamed intact platelet composition. For example, the e-beam treated platelet concentrate can be thawed and then processed as disclosed herein to prepare a platelet lysate composition, including e.g. the fibrinogen depletion and/or filtering steps disclosed above. In this regard, the thawing of the e-beam treated composition comprising a platelet concentrate can serve to lyse intact platelets, particularly in cases where the platelet composition has not, prior to the e-beam treatment while frozen, been subjected to other processes that lyse the platelets, such as prior freeze/thaw processes or activation with thrombin or other agents as discussed above. As demonstrated for example in the specific Examples below, platelet lysate prepared from e-beam treated platelet concentrate contains advantageously high levels of growth factors.

The e-beam treated platelet lysate, or the e-beam treated platelet concentrate composition or a platelet lysate prepared therefrom, can also be subjected to other steps, including for example one or more additional filtrations and/or one or more additional pathogen reduction treatments, such as a solvent-detergent pathogen reduction treatment in which the composition is contacted with an organic solvent and a detergent (e.g. nonionic detergent), followed by removal of the organic solvent and detergent (potentially but for trace amounts). The finally processed product can then be packaged in containers such as bags or vials, which preferably maintain a sterile sealed environment in which the platelet compositions reside.

A pathogen reduced platelet lysate composition or other platelet composition herein may be packaged at its full concentration as e-beam treated, or it may be diluted with water or an aqueous medium for packaging and later use, for example dilutions to 90% to 10% of the original concentration of the platelet composition can be prepared, and such diluted compositions, and their resulting corresponding reductions in the component levels specified herein, form additional embodiments disclosed herein.

Figure 2:
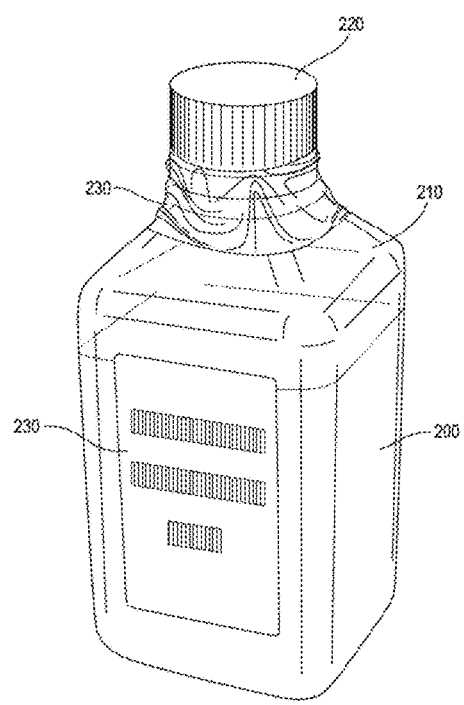
FIG. 2 provides a perspective view of one embodiment of a packaged pathogen reduced platelet composition according to the present disclosure.

One embodiment of packaging is illustrated in FIG. 2. In accordance with some forms of practice, the e-beam processed platelet lysate or other platelet concentrate composition 200 is stored in a sterile media bottle 210. Sterile media bottles may, for example, have a volume capacity in the range of 50 mL to 5000 mL. As examples, 60 mL, 125 mL, 250 mL, 500 mL, 1000 mL, or 2000 mL bottles may be used. In some forms, cap 220 of sterile media bottle 210 is protected by shrink wrap 230. In some forms, the bottle is shrink wrapped. In certain embodiments, the bottle is labeled with a finished product label 240. In some forms, the bottle is placed in a product box with dry ice.

In certain embodiments, the pathogen reduced platelet lysate or other platelet composition may be combined with other ingredients to form a cell culture medium. Such a cell culture medium comprises a platelet lysate of the present disclosure mixed with other nutrients or media for cell culture, including for example those as found in known cell culture media such as Minimum Essential Medium (MEM), or Dulbecco's Modified Eagle Medium (DMEM). A cell culture medium according to the present disclosure is formulated to provide nutrients (e.g. growth factors, etc.) necessary for the growth or maintenance of cells including for example stem and/or progenitor cells, such as mesenchymal stem cells, or immune cells such as T cells or natural killer (NK) cells. Cells cultured using the pathogen reduced platelet lysate or other platelet composition herein as or in a culture medium for the cells can in some embodiments be used medically by administering the cells to a human or other animal patient, and can have beneficial phenotypic and/or other characteristics for such administration. For example, mesenchymal or other stem cells can be administered to patients locally and/or systemically to the vasculature (e.g. by intravenous administration) for therapeutic purposes. Cultured immune cells, such as T cells, can be administered to patients to provide immunotherapy to treat cancer. In some forms, the immunotherapy is an adoptive cell transfer therapy in which a patients' own immune cells—collected from their blood or directly from their tumors—are to treat their cancer. The cancer can be melanoma, a blood cancer such as leukemia, or a lymphoma. In one mode of use, the pathogen reduced platelet lysate is used in the culture of a patient's cells conjunction with "CAR T-Cell Therapy", "TCR Therapy" or "TIL Therapy".

In CAR T-cell therapy, a patients' T cells are collected from the blood, e.g. via apheresis. The T cells are then genetically modified to express a synthetic, or man-made, protein on their surface known as a chimeric antigen receptor, or CAR. The CARs on the T cells are designed to bind to specific proteins on the surface of cancer cells. After the T cells are engineered to express a CAR, they are then grown in the laboratory, using as or in the culture medium a pathogen reduced platelet lysate as described herein, typically until there are over a hundred million of them. The CAR T cells are subsequently infused into the vascular system of the patient, usually after the patient has received chemotherapy and other drugs that deplete the body of existing T cells.

TCR therapy also involves engineering T cells collected from patients to express a receptor on their surface—called a T-cell receptor, or TCR. After the T cells are engineered to express a TCR, they are then grown, using as or in the culture medium a pathogen reduced platelet lysate as described herein, typically until there are over a hundred million of them. The TCR engineered cells are subsequently infused into the vascular system of the patient, again usually after the patient has received chemotherapy and other drugs that deplete the body of existing T cells.

In TIL Therapy, tumor-infiltrating lymphocytes (TILs) are collected from a sample of a patient's tumor and tested to identify those with the greatest ability to recognize the patient's tumor cells. The identified TILs are then grown, using as or in the culture medium a pathogen reduced platelet lysate as described herein, typically until there are over a hundred million of them. The TIL cells are subsequently activated with cytokines and then infused into the vascular system of the patient, again usually after the patient has received chemotherapy and other drugs that deplete the body of existing T cells.

In other embodiments, the pathogen reduced platelet lysate or other platelet composition can be used as a therapeutic substance. For example, the composition can be used as a therapeutic substance for medical treatments, including for treatment of diseased or damaged tissue such as nerve, tendon, bone, muscle, skin (e.g. wound healing), connective, ocular and/or cardiovascular (e.g. heart or aorta) tissue. The pathogen reduced platelet composition can be delivered, alone or in a composition with one or more other components, to these or other tissues. Delivery can be accomplished using any suitable means including for example injection or other surgical implantation or topical administration. In certain uses, in treating ocular tissue, a pathogen reduced platelet lysate composition herein is applied to the surface of an eye (e.g. in the form of liquid drops), for example in the treatment of ocular surface defects or diseases, such as ocular graft versus host disease (ocular GVHD), corneal ulcers, dry eye (Keratoconjunctivitis Sicca), or corneal repair after surgery or injury.

In accordance with certain forms, the platelet composition of the present disclosure is used to treat a mammalian patient (e.g. human, canine, feline, equine, etc.). In preferred modes of use, the platelet lysate or other platelet composition is allogeneic with respect to the treated patient, while in other embodiments the platelet lysate or other platelet composition can be xenogenic to with respect to the treated patient. For example, in certain embodiments, a pathogen reduced platelet lysate composition derived from human platelets may be used to treat a canine patient. It is also envisioned that a pathogen reduced platelet lysate composition derived from canine platelets may be used to treat a canine patient, and that a pathogen reduced platelet lysate composition derived from human platelets may be used to treat a human patient. In some forms, the human patient is suffering from Keratoconjunctivitis Sicca. In accordance with certain inventive variants, a pathogen reduced platelet lysate composition is used to treat a canine patient suffering from Keratoconjunctivitis Sicca. The canine patient may be any breed of canine, breeds commonly affected by Keratoconjunctivitis Sicca include: cavalier king charles spaniel, bulldog, Chinese shar-pei, Ihasa apso, shih tzu, west highland white terrier, pug, bloodhound, cocker spaniel, Pekingese, boston terrier, miniature schnauzer, and samoyed.

Figure 3:
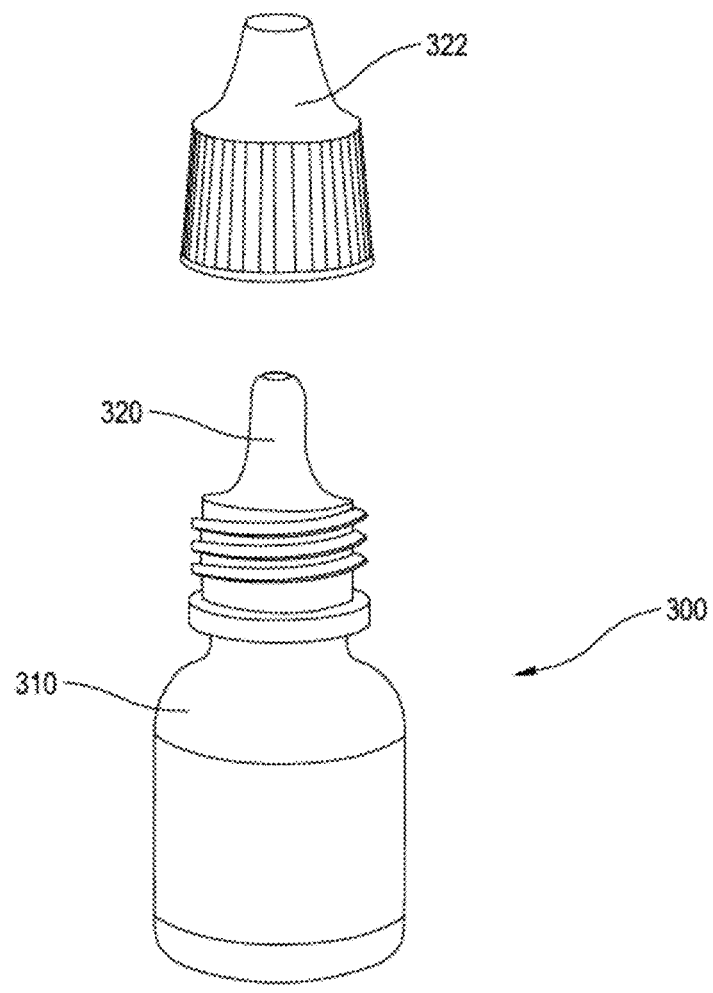
FIG. 3 provides a perspective view of one embodiment of a liquid delivery device for delivering a platelet lysate or other platelet composition as described herein.

The pathogen reduced platelet lysate can be packaged in a liquid delivery device configured to deliver the lysate to a patient's eye. In some forms, the liquid delivery device is a sterile container. FIG. 3 illustrates one embodiment of a liquid delivery device. In the illustrated embodiment the pathogen reduced platelet lysate is stored within device 300. Device 300 has a storage portion 310 and a dispersal portion 320. In the illustrated embodiment, dispersal portion 320 may optionally be covered with lid 322. Dispersal portion 320 may be configured so as to dispense a portion of the platelet lysate or other platelet composition (e.g. individual drops). In some forms, storage portion 310 comprises a deformable plastic material which can be squeezed by a user. Other suitable liquid delivery devices include but are not limited to: eye droppers, and pipettes.

In accordance with other embodiments the pathogen reduced platelet lysate or other platelet composition is formulated in an ointment. In some forms, the ointment is applied topically to an affected area (e.g. a patient's eye).

In still other uses, a pathogen reduced platelet lysate herein can be used as a cryopreservative for cells. In such cryopreservative uses, the pathogen reduced platelet lysate composition can be incorporated in a cellular suspension composition, and the cellular suspension composition can be cryopreserved to preserve the viability of the cells. The cells can be any of a variety of cells, including stem cells such as mesenchymal stem cells, progenitor cells, immune cells, or others. The cryopreservation can be conducted in a suitable vessel, such as a bag or vial.

The following specific Examples are provided to promote a further understanding of certain aspects of the present disclosure. It will be understood that these Examples are illustrative, and not limiting, in character.

Example 1

The purpose of this Example was to evaluate the effect of different electron-beam (E-beam) irradiation doses on the characterization and functionality of human platelet lysate (HPL) as a cell culture supplement. E-beam irradiation was applied to pooled frozen platelet units which were then converted to HPL. The resultant HPL was tested for growth factor levels and ability to support cell growth. This was compared to growth factor levels and cell growth support for HPL similarly prepared from frozen platelet units, except without any e-beam treatment (Controls in the Figures).

Methods

E-beam processing. A total of 120 frozen platelet units (approx. 250 mL each) were thawed at 4° C. overnight, cut open, and the contents pooled into a single 25 L blood compatible bag. From the bag of 120 thawed and pooled platelet units, 600 mL of liquid platelets were transferred to a 1 L Freeze-Pak bag. The repackaged platelet units were then frozen at −20° C., making sure that the shape of bag plus the contents was as uniformly flat to a 3 cm thickness as possible. Each frozen 600 mL platelet sample was packaged on dry ice in a cold shipper container. Packaged units were shipped to overnight to a facility for E-beam processing. The packaged units were subjected to a minimum-maximum dose range, obtained by processing each side of the 3 cm thick bags. Table 1 below shows the minimum-maximum dose ranges evaluated in this Example.

TABLE 1

| % Dose Distribution | | |
|---|---|---|
| <20% Minimum Dose | Duration (min) | >80% Maximum Dose |
| 35 | 1.35 | 47 |
| 40 | 1.35 | 54 |
| 45 | 1.35 | 61 |
| 50 | 1.35 | 68 |
| 55 | 1.35 | 74 |

Preparation of HPL. E-beam treated platelet units were converted into HPL. Generally, after thawing, the pH of the platelet units was adjusted to 7.75+/−0.25. 1.0 g/L of calcium chloride dehydrate was added to each bag to initiate clotting. The bags were then shaken at 85 RPM at room temperature and humidity for 2-hours, and then incubated at 4° C. for another 24-48 hours. Clotted material was separated from the bag, and extracted liquid was filtered through a sterilizing-grade filter.

Growth factor characterization. Growth factor measurements of the prepared HPL were performed for FGFb, PDGF-BB, PDGF-AB, EGF, and TGF-beta using ELISA kits and a microplate reader (Synergy Neo2 Plate Reader, BioTek Instruments). Growth factors for each treatment and control were analyzed in triplicate. ELISAs were performed according to manufacturer's protocol. Prior to running the ELISA, a dilution series was performed and appropriate dilutions were used for each growth factor analyzed.

Cell growth verification. In preparation for the cell growth verification assay, previously cryogenically stored Mesenchymal Stem Cells (MSCs) were thawed and plated at 5000 cells/cm$^2$ using appropriate cell culture media (DMEM supplemented with 10% HPL and 1% pen/strep/amp). After allowing the MSCs to proliferate to 70-80% confluence, cells were harvested and seeded for experiments. Cell culture testing was performed using multi-well plate. For each experiment, cells were plated in a 12-well plate at 20,000 cells/well with 1 mL of media. A media change was performed the day after seeding and the experiment was stopped after five days or when any of the samples reached 70-80% confluence. If cells failed to reach 70-80% confluence three days after the first media change, a second media change was performed on day 4.

To harvest the cells, wells were washed with 0.5 mL PBS and trypsinized with 250 µl of TrypLE for 10 minutes. Once cells were detached, 250 µl of media was added to each well to quench the TrypLE. The samples were then transferred into micro centrifuge tubes and centrifuged at 2000 g for 5 minutes. The media was then aspirated and the pellets were resuspended in 500 µl of fresh media. Total cell count for each control and treatment well were obtained using Vi-Cell XR Cell Viability Analyzer (Beckman Coulter, USA).

Statistical Analysis. The data are presented as mean±standard deviation of at least three experiments. Statistical analyses between groups were carried out using a student t-test and one-way ANOVA. $p<0.05$ was considered to indicate a statistically significant difference (*=$p<0.05$, =$p<0.001$, *=$p<0.0002$, ****=$p<0.0001$).

Results

Figure 4:
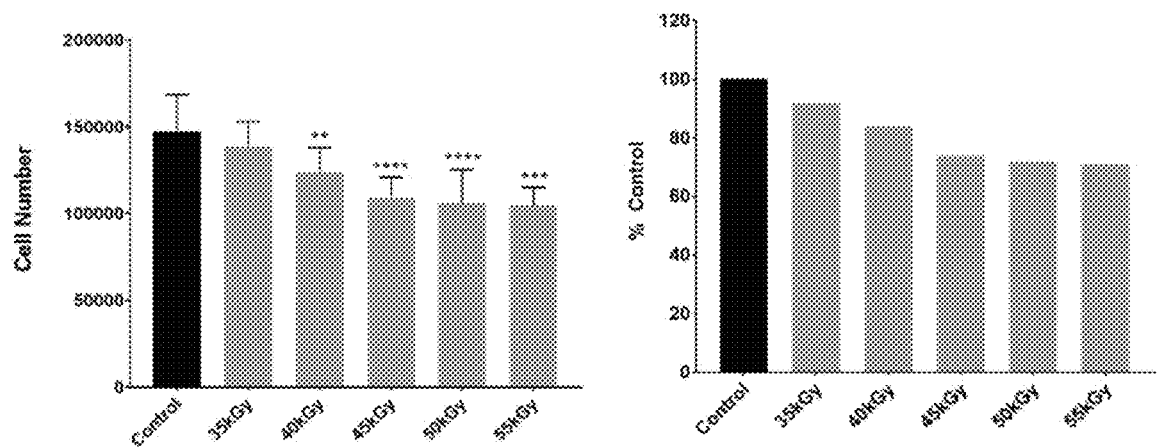
FIG. 4 provides a comparison of ASC cell growth in media supplemented with HPL processed at various minimum e-beam dose ranges. A: Cell growth analysis using cell number B: Cell growth analysis using percentage of control. The data shows ASC cell growth decreased significantly at the minimum dose range of 40 kGy and above (*=$p<0.05$, =$p<0.001$, *=$p<0.0002$, ****=$p<0.0001$). Data reported are the mean of three independent experiments of different HPL batches.
Figure 5:
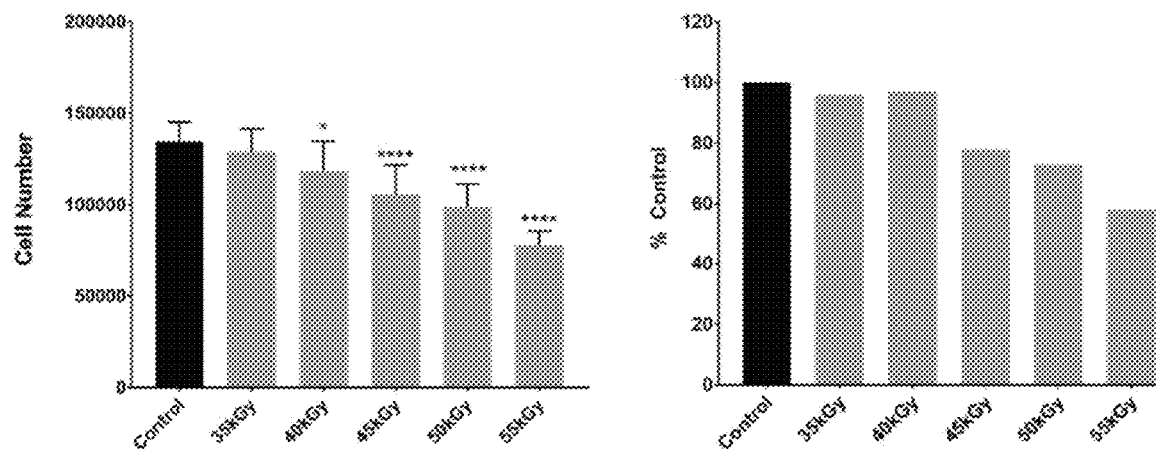
FIG. 5 provides a comparison of BM-MSC cell growth in media supplemented with HPL processed at various minimum dose ranges. A: Cell growth analysis using cell number B: Cell growth analysis using percentage of control. The data shows ASC cell growth decreased significantly at the min. dose range of 40 kGy and above (*=$p<0.05$, =$p<0.001$, *=$p<0.0002$, ****=$p<0.0001$). Data reported are the mean of three independent experiments of different HPL batches.

Cell culture performance. To examine the effects of E-Beam irradiation on MSC growth, cell growth performance was tested on two different MSCs (ASC and BM-MSC). The cells were cultured in media prepared with 10% HPL and 1% pen/strep/amp as described earlier in this Example. The results are presented in FIGS. 4 and 5. FIG. 4 provides a comparison of ASC cell growth in media supplemented with HPL processed at various minimum dose ranges. A: Cell growth analysis using cell number B: Cell growth analysis using percentage of control. The data shows ASC cell growth decreased significantly at the minimum dose range of 40 kGy and above (*=$p<0.05$, =$p<0.001$, *=$p<0.0002$, ****=$p<0.0001$). Data reported are the mean of three independent experiments of different HPL batches. FIG. 5 provides a comparison of BM-MSC cell growth in media supplemented with HPL processed at various minimum dose ranges. A: Cell growth analysis using cell number B: Cell growth analysis using percentage of control. The data shows ASC cell growth decreased significantly at the min. dose range of 40 kGy and above (*=$p<0.05$, =$p<0.001$, *=$p<0.0002$, ****=$p<0.0001$). Data reported are the mean of three independent experiments of different HPL batches. As shown, under the conditions of the present work, E-Beam irradiation began to negatively affect ASC cell growth at an irradiation dose range of 40 kGy and above, and BM-MSC cell growth is affected at a dose range of 45 kGy and above.

Figure 6:
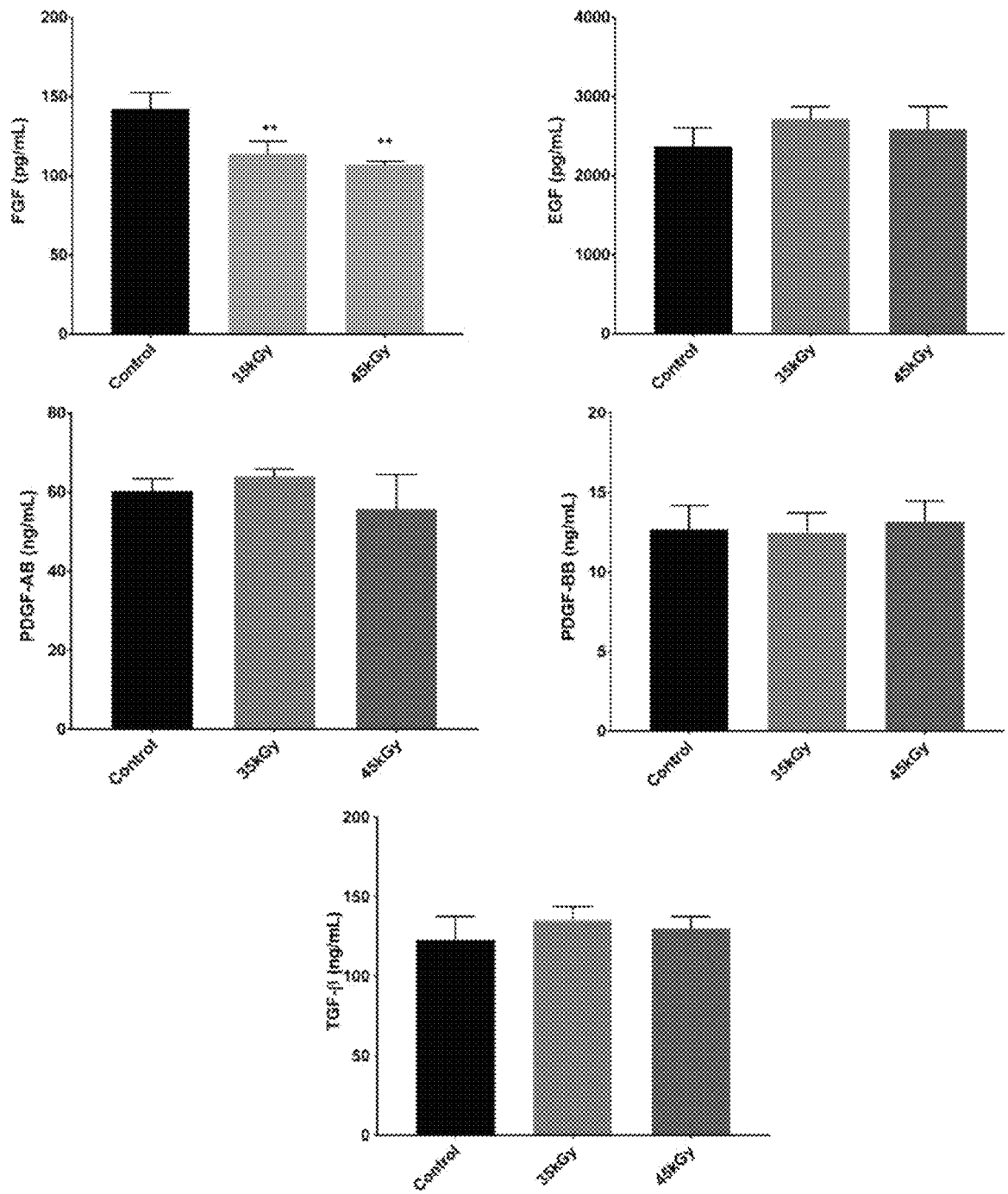
FIG. 6 shows the levels of five growth factors (FGFb, EGF, PDGF-AB, PDGF-BB, and TGF-β1) in e-beam processed and control HPL materials as determined by ELISA. Data reported are the mean of three independent experiments of different HPL batches.

Growth factor analysis. FIG. 6 provides the levels of five growth factors FGFb, EGF, PDGF-AB, PDGF-BB, and TGF-β1, known to be relevant for MSC cell growth, as determined by ELISA. Data reported are the mean of three independent experiments of different HPL batches. As shown, under the conditions of the present work, among the growth factors tested, FGFb is the most reduced by E-Beam irradiation.

Morphology. No appreciable differences were noted in morphology between cells cultured in control versus E-Beam treated material.

Example 2

The purpose of this Example was to evaluate the effect of electron-beam (e-beam) irradiation on the growth factor content of human platelet lysate (HPL) materials prepared from e-beamed platelets ("Platelets" in the Figures), or HPL e-beamed after its preparation from platelets ("Lysate" in the Figures), and the functionality of these HPL materials as a cell culture supplement for growth of ASCs and MSCs. These HPL materials were compared to a platelet lysate similarly prepared from platelets, except without any e-beam treatment (Controls in the Figures).

Methods

E-beam Processing of Platelets and HPL. A total of 240 frozen platelet units (approx. 250 mL each) were thawed at 4° C. overnight, cut open, and the contents pooled. The pooled platelet volume was then equally divided into two separate sterile plastic containers. From the first container, 6.5 L of pooled liquid platelets were transferred to each of 4×25 L Flex bags. Platelets from the second container were immediately processed to make HPL as described below. The HPL was then transferred to each of 3×25 L flex bags at 6.5 liters each. A 100 mL volume of HPL was frozen separately to serve as a control. The repackaged platelets from the first container and the processed HPL from the second container were then frozen at −20° C., making sure that the shape of each Flex bag was as close to uniformly flat as possible with a 3 cm thickness. All samples as well as the control were packaged on dry ice in a cold shipper container and were shipped to a facility for e-beam processing. The units designated for e-beam processing were subjected to a dose range of 40-54 kGy, obtained by applying directional e-beam radiation to a first side of the 3 cm thick bags while they rested upon dry ice and were conveyed through the e-beam radiation, flipping the bags on the dry ice, and then applying directional e-beam radiation to the second side of the 3 cm thick bags as the bags again rested upon the dry ice and were conveyed through the e-beam radiation. The shipping control was not e-beam processed.

Growth factor characterization. Growth factor measurements were performed using ELISA kits and a microplate reader (Synergy Neo2, BioTek Instruments). Growth factors for each treatment and control were analyzed in triplicate. ELISAs were performed according to the manufacturer's protocol. Prior to running the ELISA, a dilution series was performed and appropriate dilutions were used for each growth factor analyzed.

Cell growth verification. In preparation for the cell growth verification assay, previously cryogenically stored ASCs and MSCs were thawed and plated at 5000 cells/cm$^2$ using appropriate cell culture media. After allowing the cells to proliferate to 70-80% confluence they were harvested and seeded for experiments. Cell culture testing was performed using multi-well plates. For each experiment, cells were plated in a 12-well plate at 20,000 cells/well with 1 mL of media. A media change was performed the day after seeding and the experiment was stopped after five days or when any of the samples reached 70-80% confluence. If cells failed to reach 70-80% confluence three days after the first media change, a second media change was performed on day 4.

To harvest the cells, wells were washed with 0.5 mL PBS and trypsinized with 250 μl of TrypLE for 10 minutes. Once cells were detached, 250 μl of media was added to each well to quench the TrypLE. The samples were then transferred into micro centrifuge tubes and centrifuged at 2000 g for 5 minutes. The media was then aspirated and the pellets were resuspended in 500 μl of fresh media. Total cell counts for each control and treatment well were obtained using Vi-Cell XR Cell Viability Analyzer (Beckman Coulter, USA).

Statistical Analysis. The data are presented as mean±standard deviation of at least three experiments, except for the screening experiments that are from a single experiment. Statistical analyses between groups were carried out using a student t-test and one-way ANOVA. $p<0.05$ was considered to indicate a statistically significant difference (*=$p<0.05$, =$p<0.001$, *=$p<0.0002$, ****=$p<0.0001$).

Results

Figure 7:
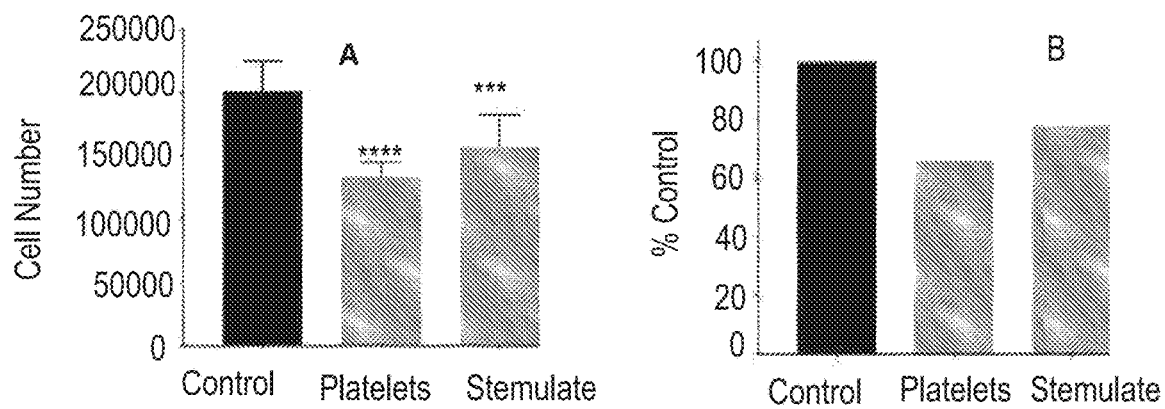
FIG. 7 provides a comparison of ASC cell growth in media supplemented with HPL processed from e-beamed platelets and e-beamed HPL. A: Cell growth analysis using cell number B: Cell growth analysis using percentage of control. (*=$p<0.05$, =$p<0.001$, *=$p<0.0002$, ****=$p<0.0001$).
Figure 8:
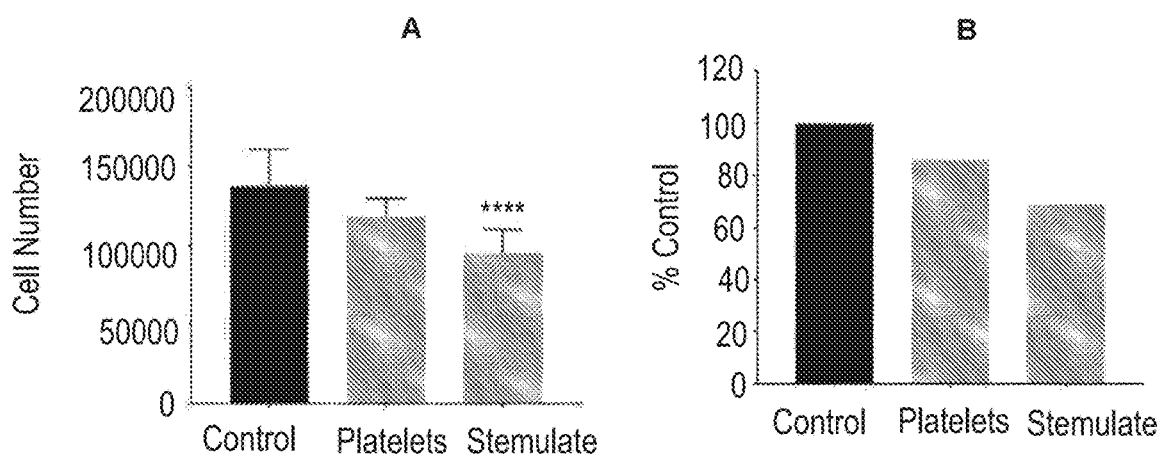
FIG. 8 provides a comparison of BM-MSC cell growth in media supplemented with HPL processed from e-beamed platelets and e-beamed HPL, versus a non-e-beamed control.

Cell culture performance. To examine the effects of E-Beam irradiation on MSC growth, cell growth performance was tested on two different MSCs (ASC and BM-MSC). The cells were cultured in media prepared with 10% HPL and 1% pen/strep/amp (DMEM) as described earlier in this Example. The results are shown in FIGS. 7 and 8. FIG. 7 provides a comparison of ASC cell growth in media supplemented with HPL processed from e-beamed platelets and e-beamed HPL. A: Cell growth analysis using cell number B: Cell growth analysis using percentage of control. (*=$p<0.05$, =$p<0.001$, *=$p<0.0002$, ****=$p<0.0001$). FIG. 8 provides a comparison of BM-MSC cell growth in media supplemented with HPL processed from E-beamed platelets and E-beamed HPL. A: Cell growth analysis using cell number B: Cell growth analysis using percentage of control (*=$p<0.05$, =$p<0.001$, *=$p<0.0002$, ****=$p<0.0001$). As shown, at the minimum-maximum dose range tested (40-54 kGy), both e-beamed platelets and HPL exhibited a beneficial capacity to support ASC and BM-MSC cell growth. Both e-beamed platelets and HPL exhibited significantly reduced ASC cell growth relative to control under the conditions tested. For BM-MSCs, a small, non-significant loss of BM-MSC growth relative to control was observed with e-beamed platelets, and a significant reduction in the growth was observed for e-beamed HPL.

Growth factor analysis. FIG. 9 shows the results of the ELISA measurements of the concentrations of five growth factors (FGFb, EGF, PDGF-AB, PDGF-BB, and TGF-beta known to be relevant for MSC growth. Data reported were the mean of three independent experiments (*=$p<0.05$, =$p<0.001$, *=$p<0.0002$, ****=$p<0.0001$). As shown, the e-beam processed materials retained beneficial levels of the growth factors tested. Under the conditions tested, the e-beam irradiation did reduce the concentration of FGFb, both in platelets and HPL. A significant rise in levels of EGF, PDGF-BB and TGF-β1 relative to control was also measured in HPL prepared from e-beamed platelets, while non-significant reductions in the levels of these growth factors was observed for e-beamed HPL.

Morphology. No appreciable differences in morphology were noted between cells cultured in control vs. e-beam treated material.

Example 3

The purpose of this Example was to evaluate the inactivation of appropriate test viruses in human platelet lysate (HPL) using e-beam radiation. The virus selected for this study is detailed in Table 2.

TABLE 2

| Virus | Family | Genome | Envelope | Size (nm) | Physico-Chemical Resistance |
|---|---|---|---|---|---|
| Bovine Viral Diarrhea Virus (BVDV) | Flavi | RNA | Yes | 50-70 | Medium |

Preparative Methods

Preparation of Platelet Units and HPL for E-beam Processing. A total of 125 frozen platelet units (approximately 250 mL each) were thawed at 4° C. overnight, cut open, and the contents pooled into a single 25 L blood compatible bag. From the bag of pooled platelet units, 3×600 mL of liquid platelets were transferred to separate 1 L cryogenic freeze storage bags (Charter Medical, Winston-Salem, NC). The 3 repackaged platelet units were then frozen at −20° C., making sure that the shape of bag+contents were as uniformly flat to a 3-cm thickness as possible. Each frozen 600 mL platelet sample was packaged on dry ice in a cold shipper container. Packaged units were shipped overnight to a facility for e-beam treatment. Platelet units designated for e-beam processing were subjected to a minimum-maximum dose range, obtained by processing each side of the 3-cm thick bags. Table 3 shows the minimum-maximum dose ranges evaluated in this study.

TABLE 3

3 cm Thick Bag
% Dose Distribution

| <20% Min Dose | DUR (minutes) | >80% Max Dose |
|---|---|---|
| 35 | 1.35 | 47 |
| 40 | 1.35 | 54 |
| 45 | 1.35 | 61 |
| 50 | 1.35 | 68 |
| 55 | 1.35 | 74 |

The remaining pooled platelets were used to prepare HPL for e-beam processing using the preparative method described in Example 1 above. As with the pooled platelets discussed above, HPL was transferred to 3×600 mL separate 1 L cryogenic freeze storage bags. The 3 HPL units were then frozen at −20° C., ensuring that shape of bag+contents were as uniformly flat to a 3 cm thickness as possible. Three bags of frozen pooled platelets were shipped overnight on dry ice to a viral processing facility where they were thawed overnight at 4° C., spiked with virus (BVDV), and frozen again, making sure they were frozen in a flat, 3-cm configuration, at −80° C. The BVDV spiked, frozen platelet samples (2 total, one for each dose range) were then shipped on dry ice in the appropriate secondary containment packaging overnight to a facility for e-beam processing. On arrival, the spiked, frozen platelet units were re-packaged in thermally insulated boxes containing dry ice for E-beam processing. The 3-cm thick platelet units were passed through the e-beam radiation 2 times, one per side. After the first e-beam pass, the thermally insulated box was opened and the platelet unit flipped over to receive the second e-beam treatment. After e-beam processing was completed, the treated samples were shipped overnight back to the viral processing facility on dry ice in secondary containment packaging. At the viral processing facility, the samples were removed from packaging and thawed overnight at 4° C. The thawed platelet units were fibrinogen depleted using $CaCl_2$ and clot separation as described in Example 1. Residual virus analysis was conducted on fibrinogen depleted platelet samples.

Along with platelet samples described above, 3 bags of frozen, fibrinogen depleted HPL (prepared as described in Example 1) were shipped to the viral processing facility. Processing of HPL samples followed the same steps as described above for frozen platelet units. Bags of HPL were thawed, spiked with virus, frozen again to a 3-cm thick, then shipped to the facility for e-beam treatment. At the e-beam facility, HPL samples were re-packaged, subject to 2 passes of e-beam radiation as described above for the platelets, re-packaged and shipped back to the viral processing facility, where virus analysis was conducted on the thawed samples.

Testing/Results

Cytotoxic/Interference Tests. Samples were tested for cytotoxic effects on indicator cells and for interference with viral infectivity. Cytotoxicity and interference testing were performed in advance of viral inactivation testing. Interference results for platelet and HPL samples are summarized in Tables 4 and 5, respectively.

TABLE 4

Interference positive control results for E-beam Platelets.

| Sample | Sample Dilution | Cytotoxicity | Mean Plaques | Interference |
|---|---|---|---|---|
| Interference Positive Control 1 | N/A | NA | 28.11 | NA |
| | 1.00E+00 | None | 12.67 | Yes |
| | 3.00E+00 | None | 23.00 | None |
| | 1.00E+01 | None | 28.67 | None |
| | 3.00E+01 | None | 28.67 | None |
| | 1.00E+02 | None | 27.67 | None |
| | 3.00E+02 | None | 34.67 | None |
| Interference Positive Control 2 | N/A | NA | 28.11 | NA |
| | 1.00E+00 | None | 18.00 | None |
| | 3.00E+00 | None | 20.67 | None |
| | 1.00E+01 | None | 28.00 | None |
| | 3.00E+01 | None | 29.00 | None |
| | 1.00E+02 | None | 27.00 | None |
| | 3.00E+02 | None | 26.00 | None |
| Interference Positive Control 3 | N/A | NA | 28.11 | NA |
| | 1.00E+00 | None | 12.67 | Yes |
| | 3.00E+00 | None | 23.67 | None |
| | 1.00E+01 | None | 26.00 | None |
| | 3.00E+01 | None | 29.67 | None |
| | 1.00E+02 | None | 31.00 | None |
| | 3.00E+02 | None | 24.67 | None |

TABLE 5

Interference positive control results for E-beam HPL.

| Sample | Sample Dilution | Cytotoxicity | Mean Plaques | Interference |
|---|---|---|---|---|
| Interference Positive Control 4 | N/A | NA | 28.11 | NA |
| | 1.00E+00 | None | 15.00 | None |
| | 3.00E+00 | None | 25.67 | None |
| | 1.00E+01 | None | 27.00 | None |
| | 3.00E+01 | None | 28.67 | None |
| | 1.00E+02 | None | 31.00 | None |
| | 3.00E+02 | None | 33.00 | None |
| Interference Positive Control 5 | N/A | NA | 28.11 | NA |
| | 1.00E+00 | None | 12.33 | Yes |
| | 3.00E+00 | None | 21.00 | None |
| | 1.00E+01 | None | 24.00 | None |
| | 3.00E+01 | None | 28.00 | None |
| | 1.00E+02 | None | 28.67 | None |
| | 3.00E+02 | None | 28.67 | None |

TABLE 5-continued

Interference positive control results for E-beam HPL.

| Sample | Sample Dilution | Cytotoxicity | Mean Plaques | Interference |
|---|---|---|---|---|
| Interference | N/A | NA | 28.11 | NA |
| Positive | 1.00E+00 | None | 16.67 | None |
| Control | 3.00E+00 | None | 25.00 | None |
| 6 | 1.00E+01 | None | 28.00 | None |
|  | 3.00E+01 | None | 37.00 | None |
|  | 1.00E+02 | None | 31.33 | None |
|  | 3.00E+02 | None | 29.33 | None |

As described above, independent viral spiking studies were performed at two points in the HPL process—early on with platelet units and at the end of the process with HPL—and the BVDV spiking virus. Viral inactivation results for platelet and HPL samples are summarized in Tables 6 and 7, respectively.

TABLE 6

Viral inactivation results (BVDV) for E-beam Platelets.

| Sample | Titer (log) | 95% CL | Sample volume (mL) | Total virus (log) | Viral Inactivation | 95% CL |
|---|---|---|---|---|---|---|
| Load | 5.41 | 0.08 | 600.00 | 8.19 | | |
| Treated Dose A | <−0.13 | 0.00 | 600.00 | <2.65 | >=5.54 | 0.08 |
| Treated Dose B | <−0.61 | 0.00 | 600.00 | <2.17 | >=6.02 | 0.08 |
| Shipping Control | 4.60 | 0.06 | 600.00 | 7.38 | 0.81 | 0.10 |
| Hold Control | 4.53 | 0.07 | 600.00 | 7.31 | 0.88 | 0.11 |
| Positive Control | 6.37 | 0.10 | | | | |
| Negative Contol | <0.70 | 0.00 | | | | |

Hold control = assay control, maintained entire duration of experiment;
Shipping control = Platelets shipped but not E-beam irradiated;
Positive control = culture media spiked with virus;
Negative control = media only

TABLE 7

Viral inactivation results (BVDV) for E-beam HPL.

| Sample | Titer (log) | 95% CL | Sample volume (mL) | Total virus (log) | Viral Inactivation | 95% CL |
|---|---|---|---|---|---|---|
| Load | 5.02 | 0.17 | 600.00 | 7.80 | | |
| Shipping Control | 4.56 | 0.07 | 600.00 | 7.34 | 0.46 | 0.19 |
| Treated Dose A | <−0.61 | 0.00 | 600.00 | <2.17 | >=5.63 | 0.17 |
| Treated Dose B | <−0.13 | 0.00 | 600.00 | <2.65 | >=5.15 | 0.17 |
| Hold Control | 4.12 | 0.18 | 600.00 | 6.89 | 0.90 | 0.25 |
| Positive Control | 6.37 | 0.10 | | | | |
| Negative Control | <0.70 | 0.00 | | | | |

Hold control = assay control, maintained entire duration of experiment;
Shipping control = Platelets shipped but not E-beam irradiated;
Positive control = culture media spiked with virus;
Negative control = media only Discussion. The viral inactivation values in Tables 6 and 7 are shown as being greater or equal a specific number. This can be interpreted as the e-beam treatment was able to inactivate a minimum of the indicated inactivation value. Testing of the spiked and e-beam treated material was performed on a representative 20 mL sub-sampling of the 600 mL sample volume. All e-beam treated samples in this study, platelets and HPL, returned no plaques from the volume tested. Testing a representative sample, and not the entire volume, even with zero plaques detected, requires a statistical calculation to calculate the viral inactivation. This calculation returns an inactivation value based on the percentage of total sample testing and the probability of not detecting virus that could be present in the remaining untested volume.

Listing of Certain Embodiments

The following provides an enumerated listing of some of the embodiments disclosed herein. It will be understood that this listing is non-limiting, and that individual features or combinations of features (e.g. 2, 3 or 4 features) as described in the Detailed Description above can be incorporated with the below-listed Embodiments to provide additional disclosed embodiments herein.

Embodiment 1. A method for making a pathogen reduced platelet composition, comprising:
irradiating a frozen composition comprising a platelet concentrate or a platelet lysate with electron beam radiation.

Embodiment 2. The method of embodiment 1, wherein the composition comprises a platelet concentrate.

Embodiment 3. The method of embodiment 1 or 2, wherein the composition comprises a platelet lysate.

Embodiment 4. The method of embodiment 2, also comprising, after said irradiating, lysing platelets of the platelet concentrate to form a platelet lysate.

Embodiment 5. The method of embodiment 1, wherein the composition comprises a platelet lysate and is essentially free of non-lysed platelets.

Embodiment 6. The method of any preceding embodiment, wherein the irradiating is conducted to apply about 10 to about 100 kGy of electron beam radiation to the frozen composition, more preferably about 30 to about 70 kGy of electron beam radiation.

Embodiment 7. The method of any preceding embodiment, wherein the electron beam radiation is applied to first side of the frozen composition and to a second side of the frozen composition opposite the first side, and preferably wherein the maximum thickness of the frozen mass between the first side and the second side is about 5 cm or less.

Embodiment 8. The method of any preceding embodiment, wherein during said irradiating the frozen composition is contained within a container, and wherein the electron beam radiation penetrates through the container and into the frozen composition.

Embodiment 9. The method of any preceding embodiment, wherein after said irradiating said composition retains at least 50% of an initial level of at least one of FGFb, EGF, PDGF-AB, PDGF-BB, and TGF-β1 present in said composition prior to said irradiating.

Embodiment 10. The method of any preceding embodiment, wherein said irradiating provides a dose of electron beam radiation effective to achieve at least a 3-Log reduction in at least one virus in the composition.

Embodiment 11. The method of any preceding embodiment, wherein the average thickness of the frozen composition is in the range of 0.5 cm to 5 cm.

Embodiment 12. The method of any preceding embodiment, wherein the electron beam radiation has an energy level of about 5 to about 15 MeV.

Embodiment 13. The method of any preceding embodiment, also comprising applying cooling to the frozen composition during the irradiating.

Embodiment 14. The method of any preceding embodiment, wherein said applying cooling comprises transferring negative thermal energy from dry ice into the frozen composition.

Embodiment 15. The method of any preceding embodiment, wherein said applying cooling comprises transferring negative thermal energy from a cooled gaseous atmosphere into the frozen composition.

Embodiment 16. The method of embodiment 10, wherein said applying cooling occurs within a mechanical freezer.

Embodiment 17. The method of any preceding embodiment, wherein the electron beam radiation is applied to a first side of the frozen composition.

Embodiment 18. The method of any preceding embodiment, wherein the frozen composition has an average thickness of about 3 cm or less.

Embodiment 19. The method of any preceding embodiment, wherein the electron beam radiation is applied to a first side of the frozen composition in a direction in which the frozen mass has an average thickness of about 5 cm or less.

Embodiment 20. The method of embodiment 19, wherein said average thickness is 3 cm or less.

Embodiment 21. The method of any preceding embodiment, wherein the irradiating comprises irradiating the frozen composition with electron beam radiation at a dose effective to achieve a reduction in a level of at least one virus in the composition.

Embodiment 22. The method of embodiment 21, wherein the reduction is at least a 3-Log reduction.

Embodiment 23. The method of embodiment 21 or 22, wherein the virus is a Bovine Viral Diarrhea Virus.

Embodiment 24. The method of any preceding embodiment, wherein the irradiating is conducted so as to provide a max/min dose ratio of about 2:1 or lower.

Embodiment 25. The method of any preceding embodiment, wherein the frozen composition has a total protein content of at least about 3 g/dL.

Embodiment 26. The method of any preceding embodiment, including, prior to said irradiating, conforming a deformable container containing the composition in liquid form to a first shape and freezing the composition with said container in said first shape to provide said frozen composition.

Embodiment 27. The method of any preceding embodiment, wherein said frozen composition has a volume of at least 50 ml, and preferably in the range of about 50 ml to about 10 L.

Embodiment 28. The method of any preceding embodiment, also comprising, after said irradiating, thawing the frozen composition to form a liquid composition.

Embodiment 29. The method of embodiment 28, also comprising, after said thawing, transferring the liquid composition to one package container or to multiple package containers.

Embodiment 30. The method of embodiment 30, wherein said transferring comprises transferring the liquid composition to multiple containers.

Embodiment 31. The method of embodiment 29 or 30, wherein said transferring is in a sterile transfer operation.

Embodiment 32. The method of any preceding embodiment, wherein the frozen composition is a frozen platelet lysate, and wherein after said irradiating the platelet lysate has:

TGF-β1 at a level of at least about 20 ng/ml, preferably in the range of about 20 to about 150 ng/ml, more preferably about 25 to about 150 ng/ml; and/or EGF at a level of at least about 1000 pg/ml, preferably in the range of about 1000 to about 4000 pg/ml EGF, more preferably about 2000 to about 3500 pg/ml; and/or FGFb at a level of at least about 50 pg/ml, preferably in the range of about 50 to about 200 pg/ml, more preferably about 75 to about 200 pg/ml; and/or PDGF-AB at a level of at least about 10 ng/ml, preferably in the range of about 10 to about 50 ng/ml, more preferably about 15 to about 40 ng/ml; and/or PDGF-BB at a level of at least about 1 ng/ml, preferably in the range of about 1 to about 15 ng/ml, more preferably about 2 to about 15 ng/ml.

Embodiment 33. The method of any preceding embodiment, wherein the frozen composition is a frozen platelet concentrate, wherein the method comprises preparing a first platelet lysate from the platelet concentrate after said irradiating, and wherein the first platelet lysate has:

TGF-β1 at a level of at least about 20 ng/ml, preferably in the range of about 20 to about 150 ng/ml, more preferably about 25 to about 150 ng/ml; and/or EGF at a level of at least about 1000 pg/ml, preferably in the range of about 1000 to about 4000 pg/ml EGF, more preferably about 2000 to about 3500 pg/ml; and/or FGFb at a level of at least about 50 pg/ml, preferably in the range of about 50 to about 200 pg/ml, more preferably about 75 to about 200 pg/ml; and/or PDGF-AB at a level of at least about 10 ng/ml, preferably in the range of about 10 to about 50 ng/ml, more preferably about 15 to about 40 ng/ml; and/or PDGF-BB at a level of at least about 1 ng/ml, preferably in the range of about 1 to about 15 ng/ml, more preferably about 2 to about 15 ng/ml.

Embodiment 34. An electron beam irradiated platelet composition, comprising:

a composition comprising a platelet concentrate or a platelet lysate, wherein the composition has been irradiated while in a frozen state with electron beam radiation (i) at a dose effective to achieve a reduction in a level of at least one virus in the composition and/or (ii) at a dose in the range of about 10 kGy to about 100 kGy.

Embodiment 35. The composition of embodiment 34, wherein said reduction is at least a 3-Log reduction.

Embodiment 36. The composition of embodiment 34, wherein said reduction is at least a 5-Log reduction.

Embodiment 37. A composition, comprising:

a biologically active platelet lysate having electron beam-induced protein modifications.

Embodiment 38. The composition of any one of embodiments 34 to 37, which has:

TGF-β1 at a level of at least about 20 ng/ml, preferably in the range of about 20 to about 150 ng/ml, more preferably about 25 to about 150 ng/ml; and/or EGF at a level of at least about 1000 pg/ml, preferably in the range of about 1000 to about 4000 pg/ml EGF, more preferably about 2000 to about 3500 pg/ml; and/or FGFb at a level of at least about 50 pg/ml, preferably in the range of about 50 to about 200 pg/ml, more preferably about 75 to about 200 pg/ml; and/or PDGF-AB at a level of at least about 10 ng/ml, preferably in the range of about 10 to about 50 ng/ml, more preferably about 15 to about 40 ng/ml; and/or PDGF-BB at a level of at least about 1 ng/ml, preferably in the range of about 1 to about 15 ng/ml, more preferably about 2 to about 15 ng/ml.

Embodiment 39. A method of culturing cells, comprising culturing the cells in a culture medium including a platelet lysate composition according to any one of embodiments 34 to 38 or prepared using a method of any one of embodiments 1 to 33.

Embodiment 40. The method of embodiment 39, wherein the cells comprise immune cells, preferably T cells or NK cells.

Embodiment 41. A method of treating a patient, comprising administering to the patient cells cultured according to a method of embodiment 39 or 40.

Embodiment 42. A method of treating a patient, comprising administering to the patient a platelet lysate composition of any one of embodiments 34 to 38 or prepared using a method of any one of embodiments 1 to 33.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method for making a pathogen reduced platelet composition, comprising:
   irradiating a frozen composition comprising a platelet lysate with electron beam radiation having an energy level of 5 MeV to 15 MeV,
   wherein the irradiating is conducted to apply 60 kGy to 100 kGy of electron beam radiation to the frozen composition,
   wherein the electron beam radiation is applied to a first side of the frozen composition and to a second side of the frozen composition opposite the first side, and
   wherein a thickness of the frozen composition between the first side and the second side is 0.5-5 cm.

2. The method of claim 1, wherein during said irradiating the frozen composition is contained within a container, and wherein the electron beam radiation penetrates through the container and into the frozen composition.

3. The method of claim 1, also comprising applying cooling to the frozen composition during the irradiating.

4. The method of claim 1, wherein the irradiating comprises irradiating the frozen composition with electron beam radiation at a dose effective to achieve a reduction in a level of at least one virus in the composition.

5. The method of claim 4, wherein the reduction is at least a 3-Log reduction.

6. The method of claim 5, wherein the virus is a Bovine Viral Diarrhea Virus.

7. The method of claim 1, wherein the irradiating is conducted so as to provide a max/min radiation dose ratio of 1:5 or lower, wherein the max/min dose ratio is a ratio of a maximum dose received by any portion of the frozen composition to a minimum dose received by any portion of the frozen composition.

8. The method of claim 1, including, prior to said irradiating, conforming a deformable container containing the composition in liquid form to a first shape and freezing the composition with said container in said first shape to provide said frozen composition.

9. The method of claim 1, also comprising, after said irradiating, thawing the frozen composition to form a liquid composition.

10. The method of claim 9, also comprising, after said thawing, transferring the liquid composition to one container or to multiple containers in a sterile transfer operation.

* * * * *